United States Patent [19]

Tedner

[11] Patent Number: 4,793,362
[45] Date of Patent: Dec. 27, 1988

[54] METHOD AND APPARATUS FOR MONITORING THE FLUID BALANCE OF THE BODY

[75] Inventor: Bo Tedner, Tjädervägen, Sweden

[73] Assignee: Karolinska Institutet, Stockholm, Sweden

[21] Appl. No.: 567,849

[22] PCT Filed: Apr. 20, 1983

[86] PCT No.: PCT/SE83/00148
§ 371 Date: Dec. 21, 1983
§ 102(e) Date: Dec. 21, 1983

[87] PCT Pub. No.: WO83/03746
PCT Pub. Date: Nov. 10, 1983

[30] Foreign Application Priority Data

Apr. 22, 1982 [SE] Sweden .................. 8202533

[51] Int. Cl.$^4$ .................. A61B 5/05
[52] U.S. Cl. .................. 128/734; 128/748
[58] Field of Search .................. 128/734, 748

[56] References Cited

U.S. PATENT DOCUMENTS 3,851,641 12/1974 Toole et al. .................. 128/734
4,008,712 2/1977 Nyober .................. 128/734

OTHER PUBLICATIONS

Hoffer et al. "Corrgelation & Whole-Body Impedance w/TBWV", J Appl Phys 27:4 1969.
Dverot et al., "Determination du Volume des Liquides ... Totale" La Presse Medicale 1970.
Taumasset, "Propriétés Bio-Éléltriques des Tissus" Trwavx Originavx 1963.

Primary Examiner—Edward M. Coven
Attorney, Agent, or Firm—Burns, Doane, Swecker & Mathis

[57] ABSTRACT

The change in body fluid is monitored by placing a pair of electrodes at spaced locations on a body, i.e. a wrist and a diametrically opposed ankle and generating two high frequency alternating currents, one of 1.5 kHz and the other 150 kHz, through the body via the electrodes. Another pair of electrodes is placed in the current path of the first pair of electrodes and connected to a detector for measuring body impedances at the two frequencies. A microprocessor calculates the change in fluid weight of the body according to the empiric formula:

$$\Delta V = k\,S\,\log \frac{Z_1 - Z_2}{Z_{1i} - Z_{2i}}$$

where
$\Delta V$ = change in fluid weight
$k$ = a proportionality constant having a negative value
$S$ = body surface area, based on the patient's weight and length
$Z_1$ and $Z_2$ = impedance at the lower frequency (for example 1.5 kHz), and respectively, the higher frequency (for example 150 kHz) at the second measuring occasion
$Z_{1i}$ and $Z_{2i}$ = corresponding impedances at the first measuring occasion (intitial values).

7 Claims, 1 Drawing Sheet

METHOD AND APPARATUS FOR MONITORING THE FLUID BALANCE OF THE BODY

BACKGROUND OF THE INVENTION

This invention relates to a method of monitoring the fluid balance of the body and to an apparatus for carrying out the method.

At many illnesses and their treatment it is of vital importance to be able to determine changes in the patient's fluid balance. For making this determination, conventionally the patient has been weighed repeatedly, and in combination therewith the liquid and foodstuff intake and the amounts of urine and of evacuation of the bowls were accurately recorded. This method is very complicated and uncomfortable both for the patient and the medical staff. The method, moreover, yields unsafe results, due to many sources of error, of which the human factor is not the least one.

OBJECTS AND SUMMARY OF THE INVENTION

The present invention proceeds on an entirely different and more direct way and eliminates the aforesaid shortcomings, in that two constant high-frequency partial alternating currents of a size innocious for the body, for example 100 μA, but with frequencies of entirely different magnitudes, for example 1.5 and, respectively, 150 kHz, are caused to pass through the body between two peripherally remote places thereof, for example a wrist and a diametrically opposed ankle, that the voltage drop between two other places each located near one of the two firstmentioned places is measured, that the voltage drop is separated into its two components of different frequency, each of which scalary represents the impedance of the body at the frequency in question, that the measuring process is repeated after a desired period, and the ratio between the differences in impedance at the two measuring occasions is evaluated so as to indicate the change in the fluid balance between the first and the second measuring occasion.

The invention proceeds from the fact that the body fluid contains substantially constant concentrations of electrolytes and, therefore, the body impedance is a measure of the fluid amount. The application of two significantly different frequencies is based on the observation, that the tissue resistance varies with the frequency, due to the fact that the current flows on different paths at different frequencies. At low frequencies, for example, the current flows substantially on paths between the cells while at high frequencies it also passes through the cells. This is explained in that the cell membranes act as capacitors and at sufficiently high frequencies behave as high-pass filters. It was found that the frequency combination 1.5 and 150 kHz yields a conception of optimum correctness of the fluid amount.

On the basis of a great number of test series, the following general relation was established empirically for the change in the fluid balance.

$$\Delta V = k S \log \frac{Z_1 - Z_2}{Z_{1i} - Z_{2i}}$$

where
$\Delta V$ = change in fluid weight
$k$ = a proportionality constant having a negative value
$S$ = body surface, based on patient's weight and length
$Z_1$ and $Z_2$ = impedance at the lower Frequency (for example 1.5 kHz) and, respectively, higher frequency (for example 150 kHz) at the second measuring occasion
$Z_{1i}$ and $Z_{2i}$ = corresponding impedances at the first measuring occasion (initial values)

BRIEF DESCRIPTION OF THE DRAWINGS

A preferred embodiment of the invention is described in the following, with reference to the accompanying drawing, in which.

DETAILED DESCRIPTION OF THE PREFERRED EMBODIMENTS

Figure 1:
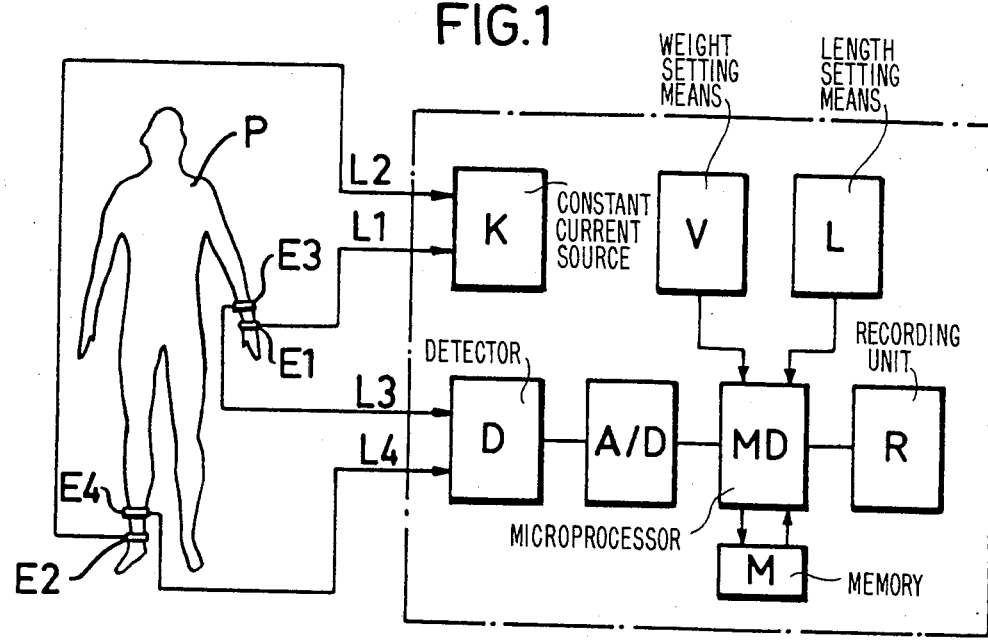
FIG. 1 is a basic diagram for the total arrangement.

According to FIG. 1, tape electrodes E1 and, respectively, E2 are applied low-resistant about the left-hand wrist and the right-hand ankle of the patient P. The electrodes are connected via flexible lines L1 and, respectively, L2 to a constant current source. At the embodiment described, the current source is capable to feed the electrodes with alternating current of 100 μA of two differently high frequencies, viz. 1.5 and 150 kHz. The measuring, of course, also can be carried out between a right-hand wrist and a left-hand ankle or even between hand and foot on the same side of the body. It is also possible to carry out local measurements, for example over only one leg or one arm in order to study the changes in fluid in the body part in question.

At a short distance (in practice about 3 cm) from the two electrodes E1, E2, two additional electrodes E3 and E4 are applied about the wrist and, respectively, ankle. The electrodes are connected via lines L3 and, respectively, L4 to a detector D. The detector is capable to sense the voltage drop between wrist and ankle and to divide the drop into its voltage components, which are of different frequency and proportional to the impedance of the body for the frequency in question. These analogous components are fed to an A/D-converter, the output of which is connected to an input on a microprocessor MD (for example type Z80). The microprocessor also has inputs for setting means V and L for the weight and, respectively, length of the patient. These means preferably are thumbwheel-operated. The processor also communicates with a memory M for storing previous measurement values or initial values. The output of the microprocessor is connected to a recording unit R, preferably in the form of a digital display with visual indication of the fluid amount in liters. When required, the display can be remote-positioned and also may be comprised in an indicator board common to several patients.

The processor processes the information received according to the above formula, which in this case applies to the frequencies 1.5 and 150 kHz. The measuring is carried out in a rapid and simple manner as follows:

When the four electrodes have been applied to the washed and defatted wrist and ankle of the patient, the patient's weight and length are set. An initial measuring is thereafter carried out for adjusting the apparatus by guidance of the digit display. Thereafter, fluid changes occurring are indicated continuously by the indicator with an accuracy of about 0.11.

Figure 2:
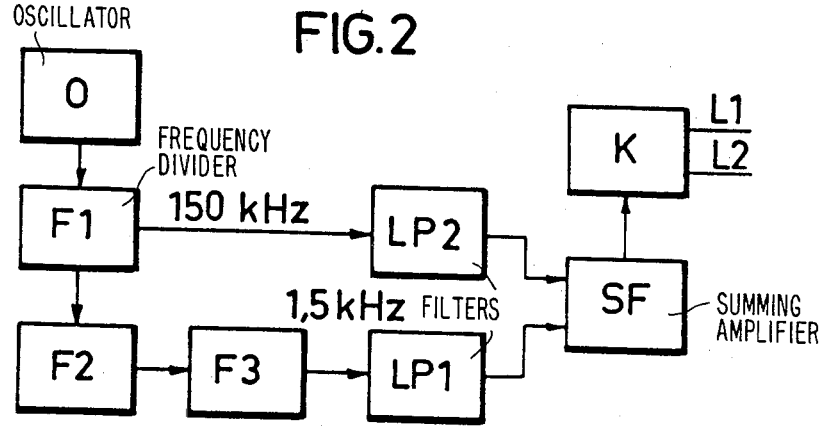
FIG. 2 is a block diagram for the current supply part.

FIG. 2 shows a suitable arrangement for the current supply. A first frequency divider F1 connected to a crystal controlled oscillator 0 of 1.5 MHz reduces the frequency by one step to 150 kHz. By means of two additional frequency dividers F2 and F3 the frequency is reduced to 1.5 kHz. The two signals of 1.5 and, respectively, 150 kHz are fed each to a low-pass filter LP1 and, respectively, LP2 for converting the ingoing square wave to a sine wave and are added in a summing-up amplifier SF and are converted to constant current in the constant current source K. The lines L1 and L2 in FIG. 1 to the electrodes should be coaxial lines, the screens driven to signal voltage by two voltage followers in order to minimize capacitive losses at the higher frequency.

Figure 3:
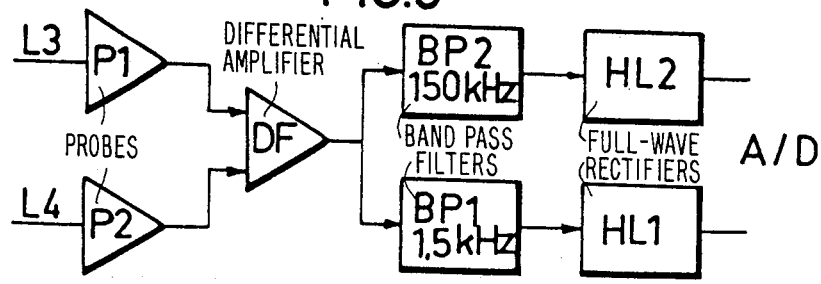
FIG. 3 is a block diagram for the detecting part.

FIG. 3 shows a suitable detection arrangement. For obtaining optimum results, high-impedance, low-noise voltage followers (input impedance about $10^{12}$ ohm) in the form of probes P1 and P2 should be mounted on the lines (L3 and L4 in FIG. 1) near the electrodes. The probes are connected to a differential amplifier DF, which feeds two parallel narrow-band band-pass filters BP1 and BP2 tuned to 1.5 and, respectively, 150 kHz. The filters are connected each to a full-wave rectifier HL1 and HL2, which detect the amplitude of the respective measuring signals being proportional to the impedance and pass it on to the A/D-converter. The measuring probes P1 and P2 have an impedance transforming function, so that the measuring is carried out high resistive on the patient. Hereby the advantage is gained that a very low measuring current flows through the patient through the skin/electrode transition, which implies that the polarization in this zone can be held low. Otherwise, the polarization would affect the measuring by disturbances in the form of varying direct voltages, especially at the low measuring frequency. The output impedance of the probes is low, below 10 ohm, so that the measuring signal can be fed loss-free to the differential amplifier DF.

The invention is not restricted to the embodiment described, but different modifications are obvious to the expert. At the expense of comfort and speed, the processor calculations and indication can be replaced by conventional calculation according to the formula. Furthermore, at least minor deviations from the preferred frequencies 1.5 kHz and 150 kHz can be made without thereby bungling the result.

I claim:

1. A method for monitoring the fluid balance of a body comprising the steps of:
(1) attaching a first pair of electrodes to the body at spaced locations to establish a path for current to pass therebetween;
(2) attaching a second pair of electrodes to the body, each located at a short distance from one of the first pair of electrodes and located in the current path between said first pair of electrodes;
(3) simultaneously passing first and second high-frequency alternating currents between said first pair of electrodes, one of said currents having a frequency on the order of 1.5 kHz and the other 150 kHz;
(4) measuring the voltage drop between said second pair of electrodes for a first measurement;
(5) separating the voltage drop into two components of different frequencies, each of which scalarly represents the impedance of the body at the respective frequency;
(6) repeating steps 4 and 5 after a desired time period for a second measurement; and
(7) calculating the ratio between the differences in impedance taken in the first measurement and the difference in impedances in the second measurement to thereby indicate a change in fluid balance of the body so that a tapping or refilling of fluid may be effected to restore fluid balance.

2. A method as defined in claim 1, wherein the change in the fluid balance is calculated by an empirically constructed formula $$\Delta V = k \, S \log \frac{Z_1 - Z_2}{Z_{1i} - Z_{2i}}$$

where
$\Delta V$ = change in fluid weight
$k$ = a proportionality constant having a negative value
$S$ = body surface area, based on the patient's weight and length
$Z_1$ and $Z_2$ = impedance at the lower frequency (for example 1.5 kHz) and, respectively, the higher frequency (for example 150 kHz) at the second measuring occasion
$Z_{1i}$ and $Z_{2i}$ = corresponding impedances at the first measuring occasion (initial values).

3. A method as defined in claim 1, wherein the spaced locations are one wrist and the diametrically opposed ankle of the body, respectively.

4. An apparatus for monitoring the fluid balance of a body comprising:
means for simultaneously generating two constant high frequency alternating currents, one of the frequencies being on the order of 1.5 kHz and the other 150 kHz;
a first pair of electrodes for attachment to the body at spaced locations so as to establish a current path therebetween, each electrode being connected to said generating means by a flexible conductor;
a second pair of electrodes for attachment to the body at locations near each electrode of the first pair of electrodes and in the current path between said first pair of electrodes;
a detector means connected to each of the second pair of electrodes by flexible conductors for dividing a sensed voltage drop into an output representative of two components of the two frequencies, each component being proportional to the impedance of the body at the respective frequency; and
means for processing the output taken during an initial measurement of the output and a second subsequent measurement of the output according to the empiric formula:

$$\Delta V = k \, S \log \frac{Z_1 - Z_2}{Z_{1i} - Z_{2i}}$$

where
$\Delta V$ = change in fluid weight
$k$ = a proportionality constant having a negative value
$S$ = body surface area, based on the patient's weight and length $Z_1$ and $Z_2$=impedance at the lower frequency (for example 1.5 kHz) and, respectively, the higher frequency (for example 150 kHz) at the second measuring occasion $Z_{1i}$ and $Z_{2i}$=corresponding impedances at the first measuring occasion (initial values).

5. An apparatus as defined in claim 4, further includes means for attaching said electrodes to one wrist and the diametrically opposed ankle of the body.

6. An apparatus as defined in claim 4, wherein the means for processing is a microprocessor connected to the detector means via and A/D-converter, with a memory means for storing a preceding or initial measuring result, said microprocessor having inputs for feeding in the weight and length of the patient from corresponding setting means and an output for connection to a recording unit.

7. An apparatus as defined in claim 6, wherein said recording unit is a digital indicator for direct digit indication of the change in fluid in liters.

* * * * *